US007011938B2

(12) United States Patent
Macey

(10) Patent No.: US 7,011,938 B2
(45) Date of Patent: Mar. 14, 2006

(54) METHOD OF MEASURING PLATELET ACTIVATION

(75) Inventor: Marion G. Macey, London (GB)

(73) Assignee: Barts and The London NHS Trust, London (GB)

( * ) Notice: Subject to any disclaimer, the term of this patent is extended or adjusted under 35 U.S.C. 154(b) by 0 days.

(21) Appl. No.: 10/415,336

(22) PCT Filed: Nov. 8, 2001

(86) PCT No.: PCT/GB01/04946

§ 371 (c)(1),
(2), (4) Date: Sep. 2, 2003

(87) PCT Pub. No.: WO02/39124

PCT Pub. Date: May 16, 2002

(65) Prior Publication Data
US 2004/0038997 A1 Feb. 26, 2004

(30) Foreign Application Priority Data
Nov. 8, 2000 (GB) ................................ 0027309

(51) Int. Cl.
*A01N 1/02* (2006.01)
*C12N 5/08* (2006.01)
*G01N 31/00* (2006.01)
*G01N 1/00* (2006.01)

(52) U.S. Cl. ........................ 435/2; 435/372; 436/18; 436/176

(58) Field of Classification Search ............... 435/2, 435/372; 436/18, 176
See application file for complete search history.

(56) References Cited

U.S. PATENT DOCUMENTS 5,817,519 A * 10/1998 Zelmanovic et al. ......... 436/63
6,309,888 B1 * 10/2001 Holvoet et al. ............... 436/71

FOREIGN PATENT DOCUMENTS

JP 08-220094 A1 * 8/1996

OTHER PUBLICATIONS

Franchi et al. "The beta-thromboglobulin test" Thromb. and Haemostasis (1980) 44(2): 107.*
Chapman et al. "The use of the anticoagulant C.T.A.D. for the assessement of ex vivo platelet activation on the ADVIA 120 haematology system" Blood (Nov. 16, 2000) vol. 96, not 11, part 2, p. 52b.*
Nagata et al. "Anticoagulants preventing pseudo-thrombocytopenia" Rinsho Byori (1992) 40(1): 87-92 (English abstract only).*
Kuhne et al. "Flow Cytometric Evaluation of Platelet Activation in Blood Collected Into EDTA vs. Diatube-H, a Socium Citrate Solution Supplememted with Theophylline, Adenosine, and Dipyradamole," Am. J. Hematol. (1995) 50: 40-45.*

* cited by examiner

*Primary Examiner*—Jean C. Witz
*Assistant Examiner*—Susan Hanley
(74) *Attorney, Agent, or Firm*—Bacon & Thomas, PLLC

(57) ABSTRACT

Platelet activation is measured by determining Mean Platelet Component (MPC) of suspended blood platelets, using a specific anticoagulant composition. The composition comprises at least one component for effecting platelet sphering (for example EDTA), and at least one platelet antagonist (for example at least one of, and preferably all three of theophylline, adenosine and dipyridamole).

32 Claims, 3 Drawing Sheets

METHOD OF MEASURING PLATELET ACTIVATION

CROSS-REFERENCE TO RELATED APPLICATION

This is a filing under 35 U.S.C. 371 of PCT/GB01/04946, filed 8 Nov. 2001, which claims priority from United Kingdom Application No. 0027309.4, filed 8 Nov. 2000.

TECHNICAL FIELD

This invention relates to the measurement of blood platelet activation, and in particular to such measurement carried out by determining so-called "mean platelet component".

BACKGROUND OF THE INVENTION

Multiple studies suggest that measurement of indicators of platelet activation might offer advantages in the clinical evaluation of patients at risk from thrombotic and other diseases (Macey, M. G., Carty, E., Webb, L., Chapman, E. S., Zelmanovic D., Okrongly, D., Rampton, D. S., Newland, A. C. (1999) "Use of mean platelet component to measure platelet activation on the ADVIA 120 Haematology System" Cytometry, 38, 250–255.; Mody, M., Lazarus, A. H., Semple, J. W. Freedman, J. (1999) "Pre-analytical requirements for flow cytometric evaluation of platelet activation: choice of anticoagulant." Transfusion Medicine 9, 147–154).

Mean platelet component ("MPC") is a parameter which can be determined by standard laboratory haematology analysers, such as the commonly used ADVIA 120™ Haematology System, produced by Bayer AG. MPC is a measure of mean refractive index of the platelets, and its value as a measure of platelet activation has been previously suggested in the Macey et al. paper referred to above. In vitro stimulation of normal platelets in whole blood by bovine thrombin resulted in activation leading to increased platelet expression of CD62P (a measure of activation) and a concomitant decrease in MPC. This response was dose and time dependent.

The ADVIA 120 Haematology System has a laser optical bench that consists of a laser diode, a flow cell and detector assemblies. A laser diode is used to produce monochromatic light focused onto the flow cell. According to the Mie Scattering Theory of light, the intensity of monochromatic light scattered at a particular angle by a uniform homogeneous sphere depends only on its volume and the average refractive index (RI) difference between the sphere and the medium in which it is suspended. This provides an equation for the intensity of monochromatic scattered light within given angular intervals that is a function of only two unknowns, volume and RI. Measuring the light scattering at two appropriate different angular intervals provides two equations with two unknowns that can be solved numerically. This is the basis of the ADVIA 120 Haematology System red blood cell and platelet measurements (Tycko, D. H., Metz, M. H., Epstein, E. A., Grinbaum, A. (1985) "Flow cytometric light scattering measurement of red cell volume and hemoglobin concentration." Applied Optics, 24, 1355–1360; Zelmanovic, D., Colella, G. M., Hetherington, E. J., Chapman, S. E., Paseltiner, L. (1998) "Automated method and device for identifying and quantifying platelets and for determining platelet activation state using whole blood samples." U.S. Pat. No. 817,519; Kunicka, J. E., Fischer, G., Murphy, J. and Zelmanovic, D. (2000) "Improved platelet counting using two-dimensional laser light scatter." American Journal of Clinical Pathology 114, 283–289).

The ADVIA 120 determines both the volume and RI of platelets on a cell-by-cell basis. Platelets intercept an incident beam of monochromatic 675±10 nm laser light emitted by a photodiode as they pass through an optical flow cell. The system measures the intensity of light scattered in the ranges of 2–3 degrees and 5–15 degrees. The pair of scattering-light intensity values is transformed into particle volume and RI values by reference to a look-up table based on the Mie Scattering Theory for homogeneous spherical particles. The platelet RI value is converted to the Mean Platelet Component (MPC) concentration, by subtracting the index of refraction of water (1.333) from RI and dividing the difference by the average refractive index increment (0.0018 dL/g) (Zelmanovic et al., 1998). This constant is derived from the weighted average refractive index increments for the major components of platelets, namely protein, lipid, and carbohydrate (Armstrong, S. H., Budka, M. J. E., Morrison, K. C., Hasson, M. (1947) "Preparation and properties of serum and plasma proteins. The refractive properties of the proteins of human plasma and certain purified fractions." Journal of the American Chemistry Society, 69, 1747–1753; Barer, R., Joseph, S. (1954) "Refractometry of living cells." Quarterly Journal of Microscopical Science, 95, 399–423; Zelmanovic et al., 1998). Recent evidence also indicates a linear relationship between platelet density (separated by stractan gradients) (Corash, L., Tan, H., Gralnick, H. (1997) "Heterogeneity of human whole blood platelet sub-populations. I. Relationship between buoyant density, cell volume, and ultrastructure." Blood, 49, 71–87) and MPC (Chapman, E. S., Lerea, K. M., Kirk, R., Sorette, M. P., Sanjay, N. S., Zelmanovic, D. (1998) "Monitoring in vitro and ex vivo platelet activity: comparison of alpha granule release, density distribution, platelet adhesion and mean platelet component concentration (MPC)." Blood, 92, Suppl. 1, 68B, Abstract 3273).

Mean platelet mass (MPM, pg) is computed from the mean PV (MPV) and MPC. Date for individual platelets may be presented in cytograms while the mean value for each parameter is tabulated (Zelmanovic, D., Colella, G. M., Hetherington, E. J., Chapman, E. S., Paseltiner, L. (1998) "Automated method and device for identifying and quantifying platelets and for determining platelet activation state using whole blood samples". U.S. Pat. No. 5,817,519).

Platelet activation occurs swiftly upon venesection or promptly afterwards, and this characteristic of platelets makes ex vivo analyses difficult. However, the extent of this in vitro activation does depend on the anticoagulant into which the blood is collected (Kuhne, T., Hornstein, A., Semple, J., Chang, W., Blanchette, V., Freedman, J. (1995) "Flow cytometric evaluation of platelet activation in blood collected into EDTA vs. Diatube-H, a sodium citrate solution supplemented with theophylline, adenosine, and dipyridamole." American Journal of Hematology,50, 40–45). For reasons of simplicity and economy, the ideal anticoagulant would be one that enabled information on platelet activation to be obtained as part of the full blood profile.

Ethylenediaminetetra-acetic acid (EDTA) as its liquid tripotassium salt is commonly used as an anticoagulant due to its availability and convenience to prepare (Perrotta, G., Roberts, L., Glazier, J., Schumacher, H. R. (1998) "Use of sodium citrate anticoagulant for routine hematology analysis on the CELL-DYN® 4000: An opportunity to enhance efficiency in the clinical laboratory." Laboratory Hematology, 4, 156–162). It is also the preferred anticoagulant for complete blood counts and white blood cell differentials because of its cell preservation properties, and is the anticoagulant recommended for these purposes by the National Committee for Clinical Laboratory Standards (NCCLS; standard H1-A4).

When monitoring platelet activation ex vivo, the main requirements are to use a venepuncture procedure that minimises spontaneous platelet activation and to collect blood into a medium that not only prevents coagulation, but will also preserve the activation status of platelets until the sample can be analysed (George J N, Thio L L, Morgan R K (1981) "Quantitative analysis of platelet membrane glycoproteins; effect of platelet washing and isolation of platelet density subpopulations." Thrombosis Research 23, 69–77; Hawiger J (1989) "Platelet secretory pathways: an overview." Methods in Enzymology 169, 191–195; Michelson A D (1996) "Flow cytometry: a clinical test of platelet function—a review." Blood 87, 4925–4936; Wu K K (1994) "Platelet activation and arterial thrombosis." Lancet 344, 991–995).

For platelet investigations EDTA is unsuitable as it causes them to swell, and experience auto-activation, which increases over time (Kuhne et al., 1995; Jackson, S. R., & Carter, J. M. (1993) "Platelet volume: Laboratory measurement and clinical application." *Blood Reviews*, 7, 104–113; McShine, R. L., Das, F. P. C., Siblinga, C. S., Brozovic, B. (1990) "Differences between the effects of EDTA and citrate anti-coagulants of platelet count and mean platelet volume." *Clinical and Laboratory Haematology*, 12, 277–285; Pidard, D., Didry, D., Kunicki, T. J., Nurden, A. T. (1986) "Temperature-dependent effects of EDTA on the membrane glycoprotein IIb/IIIa complex and platelet aggregability." *Blood*, 67, 604–611). The gradual swelling of platelets is due to alterations in the plasma membrane induced by EDTA and results in a fall in optical density and an increase in mean platelet volume (MPV). The fall in optical-density may be measured on the ADVIA 120 system (Bayer AG) as a change in the mean platelet component (MPC) (Zelmanovic et al., 1998). EDTA also alters the morphology of platelets from their innate ellipsoidal shape to spherical. Platelet shape change is a rapid reaction that can be measured either by morphologic methods such as scanning electron microscopy or by following the increase in optical density that occurs in the aggregometer. The optical technique indicates that ADP-induced shape change reaches the half-maximal optical density change in 2.5 seconds. Platelet shape change is characterised by a morphologic transformation from the normal discoid (2 to 4 $\mu$m in diameter and about 0.5 $\mu$m thick) shape to a spiny sphere containing many long, thin filopodia. This shape change begins immediately upon exposure to the anticoagulant and is maximal within 2 hr (Jackson and Carter, 1993). These changes are detectable by the ADVIA 120 after 30 minutes. Furthermore, if blood from certain individuals is anticoagulated with EDTA, the platelets aggregate, causing an apparent thrombocytopenia to be recorded (Okada T (1999) "development and problems of automatic haematology analysers." Sysmex Journal International 9, 52–57).

Therefore for platelet studies trisodium citrate has been established as the anticoagulant of choice for platelet studies (Perrotta et al., 1998). It has been demonstrated that citrate-comprising anticoagulants give rise to a lower MPV than EDTA, a trait partly explained by the preservation of normal discoid morphology (Jackson and Carter, 1993). When blood is collected in citrate, there is initially little or no change in platelet shape and volume. However, in citrate, the platelets slowly adopt a spherical shape (Macey et al., 1999) and, as in EDTA, swell progressively over a period of 1–2 h (3–10% increase in volume by impedance procedures depending on the concentration of the sodium citrate (Bath, PWM (1993) "The routine measurement of platelet size using sodium citrate alone as the anticoagulant." Thrombosis and Haemostasis 70, 687–690; Threatte G A, Adrados C, Ebbe S, Breecher G. (1984) "Mean platelet volume. The need for a reference method." *Am J Clin. Pathol*. 81: 769–72). For these reasons citrate was originally considered unreliable for the measurement of platelet volume (Thompson C B, Diaz D D, Quinn P G, Lapins M, Kurtz S R, Valeri C R. (1983). "The role of anticoagulation in the measurement of platelet volumes." *Am J Clin Pathol* 180: 327–32).

Citrate-based anticoagulants have been used for the determination of platelet parameters in the ADVIA 120 (Macey et al., 1999; Zelmanovic et al., 1998). However, the standard deviation of the MPC (recorded as platelet component distribution width (PCDW)) is initially greater in citrate than EDTA, because the light scatter characteristics of disc-shaped platelets, unlike that of spheres, is dependent on their orientation (Macey et al., 1999; Zelmanovic et al., 1998).

In previous studies it has been found that when blood anticoagulated with either sodium citrate (Maurer-Spurej, E., Pfiefer, G. Maurer, N., Linder, H., Glatter, O., Devine, D. V. (2001), "Room temperature activates human blood platelets". Lab. Invest. 81, 581–592) or acid citrate dextrose (ACD) (Oliver, A. E., Tablin, F., Walker, N. J., Crowe, J. H. (1999) "The internal calcium concentration of human platelets increases during chilling". Biochimica Biophysica Acta, 1416, 349–360) was cooled to 20° C. and 5° C. respectively the platelets were found to be activated spherical cells with pseudopodia. We have shown (unpublished data) in blood anticoagulated with sodium citrate incubated at 4° C. that there is a time dependent increase in CD62P expression on platelets and a significant increase in PLA formation.

A pilot study using the Abbott CEL L-DYN 4000™ haematology system indicates that citrate can be used instead of EDTA for routine full blood cell counts, provided that corrections are made to take account of the different dilution factor.

O'Malley et al. ("Measurement of platelet volume using a variety of different anticoagulant and antiplatelet mixtures", Blood Coagulation and Fibrinolysis 7 (4), 1996, 431–436) disclose an anticoagulant containing EDTA and theophylline for use in measuring mean platelet volume.

A relatively new anticoagulant commercially named Diatube-H™ has been developed to inhibit platelet activation and has been used for measuring plasma heparin levels and platelet factor 4 and β-thromboglobulin release from activated platelets (Kuhne et al., 1995). The main constituents of Diatube-H™ are citrate, theophylline, adenosine and dipyridamole, and it is informally termed CTAD. Theophylline and dipyridamole have been shown to inhibit phosphodiesterase activity, which leads to an increase of platelet cyclic AMP and a reduction in platelet activity. Adenosine also inhibits thrombin-induced platelet aggregation and release of intracellular calcium (Kuhne et al., 1995). Dipyridamole has the disadvantage of being light sensitive and CTAD anticoagulant tubes should be stored appropriately.

Platelets in EDTA approximate homogeneous spheres for the purposes of applying Mie theory and obtaining accurate volume and MPC values on a cell-by-cell basis (Zelmanovic et al., 1998). However, because of the platelet activating property of EDTA it is generally thought to be highly unsuitable for use as an anticoagulant for measuring patient platelet activation status.

Measurement of neutrophil activation is also of clinical importance. Neutrophils show little or no evidence of activation (e.g. by their level of CD11b expression) if analysed in whole anticoagulated blood shortly after venesection. Unfortunately, both EDTA and citrate decrease the $Ca^{2+}$ concentration in plasma and consequently affect the antigenicity of $Ca^{2+}$ dependent epitopes such as CD11b. An alternative reagent, Cyto-Chex™ (Streck Laboratories, Omaha, Nebr., USA), that is recommended for the preservation of whole blood, stabilises antigen expression on lymphocytes and neutrophils but little is yet known of its effect on platelets.

SUMMARY OF THE INVENTION

We have now discovered that, surprisingly, EDTA and similar anticoagulants generally thought unsuitable for such applications may be employed for platelet activation studies, provided that use is also made of a suitable platelet antagonist, such as those employed in CTAD.

We have also discovered that holding blood anticoagulated with such mixtures at low temperatures may reduce platelet activation over a period of hours compared with samples at ambient temperature. This is in contrast with the known increase in platelet activation in citrate or acid citrate dextrose on cooling discussed above.

Further, we have discovered that such mixtures effectively inhibit neutrophil activation in anticoagulated blood.

Accordingly, the present invention provides a blood anticoagulant composition comprising a component for effecting platelet sphering (for example a chelating agent such as EDTA or [Ethylene-bis(oxyethylenenitrilo)]tetraacetic acid ("EGTA")), and a platelet antagonist. The terms EDTA and EGTA as used herein are intended to include salts and derivatives thereof.

The component for effecting platelet sphering and the platelet antagonist may be mixed before addition of the blood sample, or may be mixed after addition of the blood sample to one of the components.

The platelet antagonist may preferably include two or more of citrate, theophylline, adenosine and/or 2-chloroadenosine and dipyridamole, more preferably three or more, and highly preferably all of citrate, theophylline, adenosine and/or 2-chloroadenosine and dipyridamole. The preferred concentrations of citrate, theophylline, adenosine and dipyridamole are generally as disclosed in a paper by Contant et al (Thrombosis Research 31: pp365–374, 1983), and in particular, within the following ranges theophylline 7.5–22.2 mM
adenosine 0.01 mM–3.7 mM
dipyridamole 0.001–2 mM, preferably about 0.02 mM
citric acid 0.1 M–0.258 M, preferably about 0.11 M The pH of the composition is preferably from 4.5 to 6.4, preferably about 5.0.

The platelet antagonist may preferably include a chelating agent. The chelating agent preferably includes one or both of EDTA and EGTA.

The blood anticoagulant composition may preferably comprise EDTA and CTAD.

The invention also provides a method of measuring platelet activation, comprising determining refractive index of blood platelets suspended in a composition comprising at least one component for effecting platelet sphering, and at least one platelet antagonist as described herein.

Techniques for determining MPC via refractive index are well known per se, and are discussed, for example in the Macey et al. 1999 paper mentioned above, as well as elsewhere in the literature. Refractive index determination is preferably carried out by measuring forward light scatter at two different angles, more preferably at angles of 2–3 degrees and 5–15 degrees.

In the method according to the present invention, refractive index determination is preferably carried out between 30 and 60 minutes post-venesection.

In the method according to the present invention, an anticoagulated blood sample is preferably maintained at a temperature of 0° C. to 10° C. between venesection and measuring platelet activation. When an anticoagulated blood sample is held in this temperature range, refractive index determination may be carried out up to 6 hours post-venesection, and is preferably carried out up to 3 hours post-venesection.

The invention also provides the use of a blood anticoagulant composition as described herein to maintain a blood sample in an anticoagulated state between venesection and measurement of platelet activation.

The invention also provides a method of measuring leucocyte activation, comprising measuring a leucocyte activation indicator of leucocytes suspended in a composition comprising at least one component for effecting platelet sphering, and at least one platelet antagonist as described herein.

A preferred embodiment of the invention is described in the following Examples.

BRIEF DESCRIPTION OF THE DRAWINGS

Reference is made in the Examples which follow to the accompanying drawings, in which:

FIG. 1 shows results of Example 1.

FIG. 2 shows results of Example 1.

FIG. 3 shows results of Example 3.

DETAILED DESCRIPTION

The invention is illustrated and/or supported by the following examples which are not intended to limit the invention in any way.

EXAMPLE 1

Comparison of E/C with EDTA and CTAD

Materials and Methods

Materials. Tyrodes salt solution (TS) was from Sigma (CaCl 2H$_2$O 0.265 g/L, MgCl 6H$_2$O 0.214 g/L, KCl 0.2 g/L, Na H$_2$CO$_2$ 1.0 g/L, NaCl 8.0 g/L, NaPO$_4$ 0.05 g/L, glucose 1.0 g/L). EDTA and CTAD in Vacutainer™ containers were from Becton Dickinson. The latter were stored in light protective boxes and removed immediately prior to use.

Antisera. IgG1-FITC, IgG1-PE, CD62P-FITC and CD45-RPE were from Immunotech. Mouse IgG2a-FITC and CD42a-FITC were from Becton Dickinson.

Blood Samples. Normal blood samples (n=6). Median age 35, 4 male, 2 female.

Assessment of platelet activation on the ADVIA 120. Whole blood samples were taken into Vacutainer™ containers (Becton Dickinson) containing either EDTA, CTAD, or a mixture of EDTA and CTAD (E/C). Samples were analysed immediately post-venesection and at timed intervals of 30, 60, 120, and 180 minutes post venesection. Analysis of platelet count (PLT), mean platelet volume (MPV), mean platelet component (MPC) and mean platelet component distributionwidth (PCDW) was performed using the ADVIA 120 Haematology System (Bayer Corporation, Tarrytown, N.Y.) calibrated prior to use with ADVIA TESTpoint Haematology Control reagents. (Bayer Corporation, Tarrytown, N.Y.).

Measurement of the expression CD62P and the number of leucocyte platelet aggregates (PLAs). Anti-coagulated blood (5 µl) was incubated at room temperature with either FITC CD62P (5 µl) or FITC isotype control (5 µl), or PE CD45 (5 µl) and FITC isotype control (5 µl) or FITC CD42a (5 µl) and PE CD45 (5 µl), in 90 µl of TS for 5 min. Samples were diluted to 1 ml with TS and analysed immediately by flow cytometry.

Flow cytometry. Blood cells were analysed on a FACScan (Becton Dickinson, Oxford, UK) equipped with CellQuest® software. The flow cytometer was calibrated prior to use with fluorochrome labelled beads (Fluorospheres™, Dako).

Figure 1:
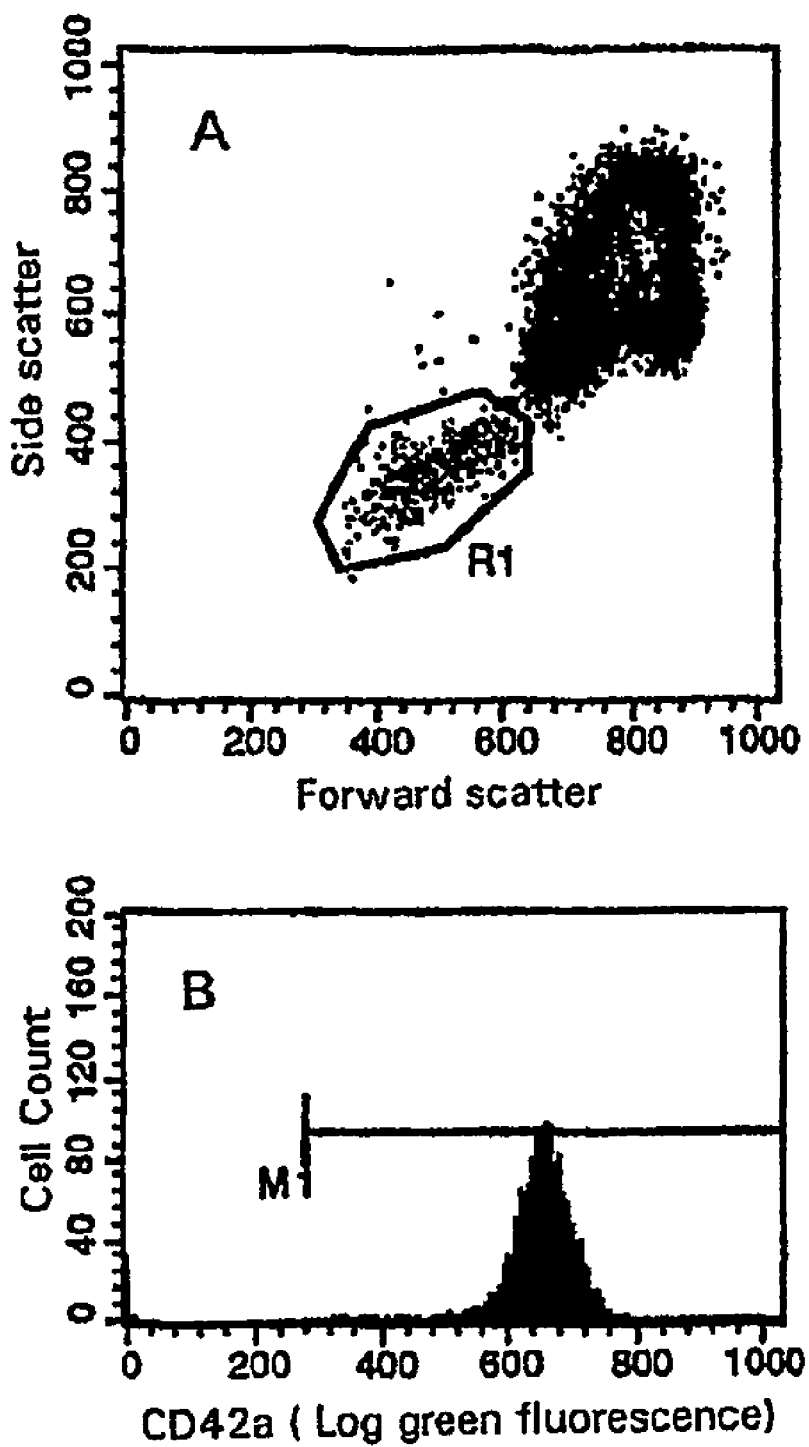
FIG. 1 shows the analysis of platelets in whole blood. Platelets in region R1 were identified by their low forward and side scatter properties (histogram A) and confirmed by the analysis of green fluorescence associated with the binding of CD42a (histogram B).

For the analysis of CD62P expression data was acquired in real time with a primary gate set on a dual parameter histogram of forward light scatter (FLS) logarithmic scale (abscissa) and side light scatter (SLS) logarithmic scale (ordinate). This facilitated identification of the platelets within the blood and was confirmed by the analysis of CD42a expression (FIG. 1). Background fluorescence was assessed with platelets labelled with the FITC conjugated isotype control antibody. Cursors were set in a single parameter histogram of frequency (ordinate) and green fluorescence intensity (abscissa), so that less than 1% of the platelets stained positively with the control antibody. Changes in CD62P expression (green fluorescence logarithmic scale), together with those of FLS and SLS, were then recorded on the gated platelets.

Figure 2:
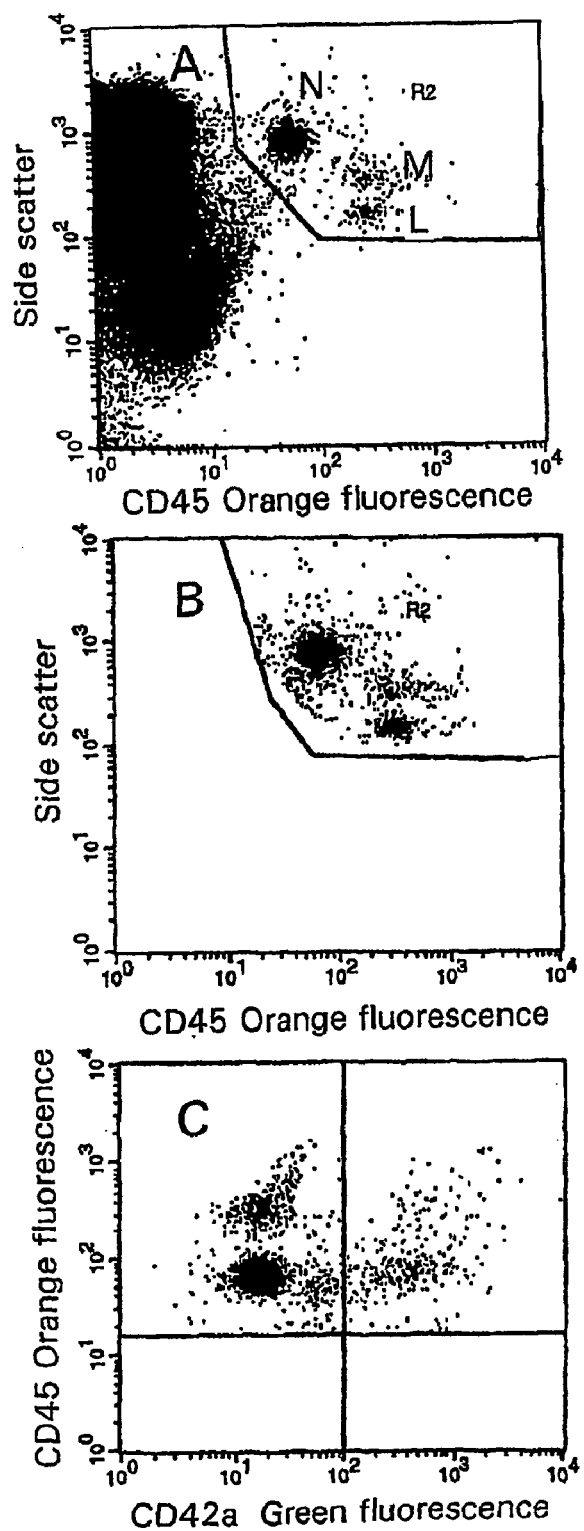
FIG. 2 shows the analysis of platelet leucocyte aggregates in whole blood. Leucocytes are identified in a plot of side scatter (logarithmic scale ordinate) versus orange fluorescence. (histogram A). Non-leucocyte events were gated out (histogram B). Leucocytes identified by their positive staining with PE CD45 were gated to a histogram of green fluorescence (logarithmic scale ordinate) and orange fluorescence (logarithmic scale abscissa) (histogram C). Events that were both green and orange were considered platelet leucocyte aggregates.

For the analysis of platelet-leucocyte aggregates (FIG. 2), cells were analysed in a histogram of side scatter (logarithmic scale ordinate) and orange fluorescence (logarithmic scale abscissa). Leucocytes identified by their positive staining with PE CD45 were gated to a histogram of green fluorescence (logarithmic scale ordinate) and orange fluorescence (logarithmic scale abscissa). Events that were both green and orange were considered platelet leucocyte aggregates and recorded as a percentage of a total of 10,000 gated leucocytes.

Statistical analysis. Platelet CD62P expression, platelet-leucocyte aggregates and MPC were compared using parametric statistics (Student's paired t-test) employing tailed p values.

Results

% CD62P Positive Platelets

| Time/min | CD62P % expression in blood anticoagulated with EDTA | CD62P % expression in blood anticoagulated with CTAD | CD62P % expression in blood anticoagulated with E/C |
|---|---|---|---|
| 0 | 1.10 ± 0.24 | 1.22 ± 0.26 | 1.28 ± 0.37 |
| 30 | 3.71 ± .04 | 1.42 ± 0.37 | 2.01 ± 0.61 |
| 60 | 11.27 ± .60 | 3.09 ± 0.84 | 5.94 ± 2.90 |
| 90 | | | |
| 120 | 18.94 ± 2.53 | 2.38 ± 0.29 | 6.98 ± 1.48 |
| 150 | | | |
| 180 | 23.05 ± 2.79 | 4.14 ± 0.61 | 8.45 ± 0.86 |

The % of CD62P positive platelets in the six subjects were low at 0 minutes (1.10±0.24%, mean±se). At 180 minutes the CD62P % values rose significantly in all three anticoagulants (p<0.02), but to a greater extent in EDTA (23.05±2.79%). In CTAD anticoagulated blood the least activation was observed (4.14±0.61%), whilst the E/C anticoagulated blood had intermediate platelet activation (8.45±0.79%). The expression of CD62P in EDTA anticoagulated blood was significantly higher (p<0.01) than in CTAD anticoagulated blood after 60 minutes.

| | Platelet-leucocyte aggregate formation | | |
|---|---|---|---|
| Time/min | % platelet leucocyte aggregates in blood anticoagulated with EDTA | % platelet leucocyte aggregates in blood anticoagulated with CTAD | % platelet leucocyte aggregates in blood anticoagulated with E/C |
| 0 | 3.50 ± 0.50 | 3.95 ± 0.73 | 2.82 ± 0.67 |
| 30 | 4.16 ± 0.86 | 5.57 ± 1.36 | 3.13 ± 0.86 |
| 60 | 8.87 ± 1.54 | 9.64 ± 1.41 | 4.48 ± 0.94 |
| 90 | | | |
| 120 | 8.50 ± 1.44 | 15.80 ± 2.15 | 6.18 ± 2.28 |
| 150 | | | |
| 180 | 13.50 ± 2.41 | 18.88 ± 3.38 | 7.81 ± 1.52 |

The platelet-leucocyte aggregates (PLAs) at 0 minutes were detectable in all subjects and they were present in greater numbers in blood anticoagulated with EDTA (3.50±0.50%, mean±se) and CTAD (3.95±0.73%), than in that anticoagulated with E/C 2±0.67%). The percentage of PLAs in CTAD anticoagulated blood increased at 180 minutes (18.88±3.38%) and this was significantly greater than the number detected in blood collected in EDTA (13.50±2.41%, p<0.05) and E/C (7.81±1.52%, p<0.02).

Platelet Count (PLT)

| Time/min | Platelet count in blood anticoagulated with EDTA | Platelet count in blood anticoagulated with CTAD | Platelet count in blood anticoagulated with E/C |
|---|---|---|---|
| 0 | 235 ± 12 | 229 ± 12 | 230 ± 13 |
| 30 | 246 ± 14 | 230 ± 13 | 237 ± 13 |
| 60 | 249 ± 14 | 234 ± 13 | 239 ± 13 |
| 90 | | | |
| 120 | 247 ± 14 | 230 ± 12 | 232 ± 11 |
| 150 | | | |
| 180 | 246 ± 5 | 225 ± 6 | 225 ± 9 |

All platelet counts in EDTA anticoagulated blood for the subjects were in the normal range, with mean±se of 235±12. There were no significant changes in platelet counts over the 180 minute period. The platelet counts in blood anticoagulated with CTAD and E/C when corrected for dilution. (dilution factor=1.11 and 1.125 respectively) were found to be similar to those in EDTA anticoagulated blood.

Mean Platelet Volume (MPV)

| Time/min | MPV in blood anticoagulated with EDTA | MPV in blood anticoagulated with CTAD | MPV in blood anticoagulated with E/C |
|---|---|---|---|
| 0 | 8.0 ± 0.37 | 9.1 ± 0.24 | 9.0 ± 0.24 |
| 30 | 7.7 ± 0.27 | 8.4 ± 0.24 | 8.6 ± 0.32 |
| 60 | 7.7 ± 0.24 | 8.5 ± 0.27 | 8.7 ± 0.30 |
| 90 | | | |
| 120 | 8.0 ± 0.30 | 8.9 ± 0.28 | 9.0 ± 0.28 |
| 150 | | | |
| 180 | 8.1 ± 0.21 | 9.2 ± 0.20 | 9.2 ± 0.28 |

The MPV value fell between 0 minutes to 30 minutes in each of the three different anticoagulants, reflecting the fact that any platelet measurement in whole blood made on the ADVIA 120 within 30 minutes of venesection will not be stable because platelet sphering is occurring during this period. The MPV was most stable between 30 and 60 minutes and then increased by a small amount in all three anticoagulants at 180 minutes. The platelet volume increased in E/C anticoagulated blood from 9.0±0.24 fL to 9.2±0.28 fL (mean±se), in EDTA from 8.0±0.37 fL to 8.1±0.21 fL and CTAD from 9.1±0.24 fL to 9.2±0.20 fL respectively.

Mean Platelet Component (MPC)

| Time/min | MPC in blood anticoagulated with EDTA | MPC in blood anticoagulated with CTAD | MPC in blood anticoagulated with E/C |
|---|---|---|---|
| 0 | 28.0 ± 0.87 | 25.2 ± 0.62 | 25.6 ± 0.54 |
| 30 | 29.1 ± 0.52 | 27.1 ± 0.40 | 26.6 ± 0.66 |
| 60 | 28.8 ± 0.42 | 26.7 ± 0.40 | 26.4 ± 0.64 |
| 90 | | | |
| 120 | 27.9 ± 0.48 | 26.3 ± 0.67 | 25.4 ± 0.67 |
| 150 | | | |
| 180 | 27.1 ± 0.36 | 25.2 ± 0.40 | 25.0 ± 0.67 |

EDTA gave rise to the highest MPC values and the decrease in MPC over 180 minutes was also greatest in blood with this anticoagulant (28.0±0.87 g/dl to 27.1±0.36 g/dl, mean±se). The lowest MPC values were observed in E/C anticoagulated blood at each time interval. In CTAD anticoagulated blood the MPC was most stable, with no change in mean MPC between 0 minutes and 180 minutes (25.2±0.62 g/dl and 25.2±0.40 g/dl respectively). The mean MPC values increased from 0 to 30 minutes and then decreased subsequently in all three anticoagulants. Lower MPC values at 60 minutes than at 30 minutes were observed in all anticoagulants, however this was most noticeable in CTAD (27.1±0.40 g/dl to 26.7±0.40 g/dl).

Platelet Component Distribution Width (PCDW).

| Time/min | PCDW in blood anticoagulated with EDTA | PCDW in blood anticoagulated with CTAD | PCDW in blood anticoagulated with E/C |
|---|---|---|---|
| 0 | 5.85 ± 0.28 | 7.41 ± 0.13 | 7.35 ± 0.21 |
| 30 | 5.00 ± 0.09 | 7.21 ± 0.13 | 6.87 ± 0.38 |
| 60 | 5.00 ± 0.12 | 7.26 ± 0.15 | 7.02 ± 0.42 |
| 90 | | | |
| 120 | 4.80 ± 0.11 | 7.53 ± 0.15 | 7.5 ± 0.44 |
| 150 | | | |
| 180 | 4.80 ± 0.06 | 7.80 ± 0.11 | 6.97 ± 0.43 |

This parameter varied between anticoagulants. CTAD gave higher PCDW values and over 180 minutes this anticoagulant caused a small rise in PCDW (7.41±0.13 g/dl to 7.80±0.11 g/dl, mean±se). In contrast mean values for EDTA and E/C anticoagulated blood decreased over time, although there was a much greater decrease in EDTA (5.85±0.28 g/dl to 4.80±0.08 g/dl) than E/C (7.35±0.21 to 6.97±0.43).

The results demonstrate that CTAD is a very good inhibitor of platelet activation, even in the presence of a platelet activating agent such as EDTA. CD62P expression did not increase upon exposure to CTAD or over a three hour time period in contrast to the other anticoagulants. Between 60–120 minutes the CD62P expression fell in CTAD; the reason for this is not clear but may be due to loss of CD62P from the platelet surface or adherence of activated platelets to the tube wall, or to other leucocytes in the blood. This latter theory is supported by the marked increase in platelet-leucocyte aggregates measured in CTAD anticoagulated blood compared to those in EDTA or E/C, and the small decrease in platelet count observed in CTAD anticoagulated blood. The reason for this is not immediately apparent but would appear to be related to the presence of EDTA which is a better chelator of calcium than citrate, and calcium is required for platelet activation to occur. Platelets contain large quantities of adenosine diphosphate (ADP), which is released in the presence of calcium upon activation; ADP can be degraded into adenosine by leucocytes (Faint, R. W. (1992) Platelet-neutrophil interactions: Their significance. *Blood Reviews*, 6, 83–91) which then has an inhibitory effect on both platelet and neutrophil activation (Seis, W. (1989) Molecular mechanisms of platelet activation. *Physiology Review*, 69, 58–65). Leucocytes and vascular endothelium express sufficient ectonucleotidases to metabolise most of the circulating nucleotides in flowing blood (Coade, S B., Pearson, J. D. (1989) Metabolism of adenine nucleotides in human blood. *Circulation Research*, 65, 531–537) but under the static conditions of the Vacutainer™ containers this metabolism may be sub-optimal leading to the presence of greater than normal levels of ADP. It is known that ADP leads to swelling of platelets and advocates platelet membranes to attach to each other (Faint, 1992), therefore it is possible that the large quantities of ADP enhance the ability of platelets and leucocytes to form aggregates. It may be therefore that the apparent inhibition of platelet activation as measured by CD62P expression, in CTAD anticoagulated blood, is an artefact due to the fact that activated platelets, although present, were not detectable because they were attached to leucocytes. It appears that ex vivo platelet-leucocyte aggregate formation is anticoagulant dependent.

EDTA is known to cause artefacts in blood, and it has been shown that in EDTA anticoagulated blood at room temperature the MPV was on average 23% greater than in the corresponding citrate anticoagulated blood (Threatte et al., 1984). This study also showed that the greatest increase in MPV in EDTA anticoagulated blood occurred within minutes of exposure. However we have shown that the MPV in EDTA, CTAD and a mixture of EDTA and CTAD fell between 0–30 minutes. These results are contrary to previous findings, and this may be related to the way in which blood was analysed. In this study the ADVIA 120 Haematology System (Bayer, Tarrytown, N.Y.) was used and this measures light scattered by the platelets at high and low angles, the former is related to the refractive index of the platelets i.e. the measure of granulation or the degree of platelet activation, and the latter is contingent upon the volume of the cells (Zelmanovic et al., 1998). Whereas, Threatte et al., used an Ultra-Flo 100 Whole Blood Platelet Analyser (Clay-Adams, Parsippany, N.J.), which is a semi-automated instrument that allows the detection of small current changes generated by the cells suspended in a conducting diluent, as they flow through an aperture (Guthrie, D. L., Lam, K. T., Priest, C. J. (1980) Ultra-Flo 100 platelet counter—a new approach to platelet counting. *Clinical and Laboratory Haematology*, 2, 231–242).

The Macey et al. 1999 paper referred to above demonstrates that in vitro stimulation of platelets in whole blood leads to an increased CD62P expression and a concurrent decrease in MPC. The above results demonstrate clearly that the MPC decreased in EDTA more than in CTAD or a mixture of EDTA and CTAD, confirming that EDTA causes platelet activation. In CTAD anticoagulated blood the mean MPC value did not change over time, hence the platelets were stable, consistent with the stable CD62P expression measured by fluorescent flow cytometry. In CTAD and mixture of EDTA and CTAD anticoagulated blood the MPC values were similar over the 180 minute period.

The high MPV and low MPC in samples employing of EDTA and CTAD mixture indicates that the platelets are sphered, to a sufficient extent for the MPC determination to be satisfactory, without undergoing degranulation. This is confirmed by the low level of expression of CD62P on platelets in EDTA/CTAD mixture anticoagulated blood, which was comparable to that on platelets in blood anticoagulated with CTAD alone. In contrast platelets in EDTA anticoagulated blood had a high MPV and high expression of CD62P showing that they had swollen and degranulated. This latter finding is in accord with previous reports .(McShine et al, 1990; Kuhne et al, 1995; Thompson, C. B., Diaz, D. D., Quinn, P. G., Lapins, M., Kurtz, S. R., Valeri, C. R. (1983) The role of anticoagulation in the measurement of platelet volumes. *American Journal of Clinical Pathology*, 80, 327–332; and Macey et al, 1999)

EXAMPLE 2

Comparison of E/C with EDTA/citric Acid, EDTA/adenosine, EDTA/dipridamole and EDTA/theophylline Materials and Methods Preparation of Platelet Drugs The platelet activation controlling drugs were used in combination with 0.11M citric acid (Sigma, Steinheim, Germany); they were as follows; 3.7 mM adenosine (Sigma, Steinheim, Germany), 0.198 mM dipyridamole (Sigma, Belgium) and 15 mM theophylline (Sigma, Steinheim, Germany). The pH of each solution was adjusted if necessary to pH 5.0. The solutions were filter sterilised and stored at $-20°$C. until needed. The anticoagulant CTAD (Becton Dickinson, Plymouth, UK) was stored in light protective boxes and removed prior to use.

Materials.
As Example 1.

Antisera.
As Example 1.

Blood Collection
Blood was drawn from the antecubital vein of 5 volunteers (mean age 38, 3 female and 2 male) into four EDTA Vacutainer™ containers (Becton Dickinson, Plymouth, UK) using a 21-gauge needle. Three EDTA samples were added to Vacutainer™ containers containing citric acid with either adenosine or dipyridamole or theophylline. The final EDTA sample was added to a Vacutainer™ containing the anticoagulant CTAD.

Assessment of Platelet Activation on the ADVIA 120
Whole blood samples were taken into Vacutainer™ containers (Becton Dickinson) containing EDTA and mixed with the aforementioned platelet antagonists, or with CTAD (this mixture is referred to as E/C). Samples were analysed as in Example 1.

Measurement of the Expression CD62P and the Number of Leucocyte Platelet Aggregates (PLAs).
As Example 1.

Flow Cytometry.
As Example 1.

Statistical Analysis
The paired t test was applied to determine differences between the four anticoagulant mixtures studied.

Results

| | Platelet count | | | |
|---|---|---|---|---|
| Time/min | Platelet count in blood anticoagulated with E/A/$10^9$/l | Platelet count in blood anticoagulated with E/D/$10^9$/l | Platelet count in blood anticoagulated with E/T/$10^9$/l | Platelet count in blood anticoagulated with E/C/$10^9$/l |
| 0 | 269 ± 17.58 | 246 ± 15.18 | 241 ± 12.10 | 267 ± 21.84 |
| 30 | 266 ± 16.51 | 262 ± 15.69 | 257 ± 13.09 | 264 ± 20.41 |
| 60 | 270 ± 18.55 | 269 ± 21.18 | 262 ± 17.20 | 268 ± 18.68 |
| 90 | | | | |
| 120 | 267 ± 14.70 | 260 ± 18.08 | 256 ± 18.77 | 257 ± 20.23 |
| 150 | | | | |
| 180 | 266 ± 16.74 | 262 ± 19.61 | 253 ± 13.00 | 259 ± 20.57 |

The platelet counts were similar and within the normal range in each of the four anticoagulant combinations.

Mean platelet volume

| Time/ min | MPV in blood anticoagulated with E/A/fl | MPV in blood anticoagulated with E/D/fl | MPV in blood anticoagulated with E/T/fl | MPV in blood anticoagulated with E/C/fl |
|---|---|---|---|---|
| 0 | 9.4 ± 0.36 | 9.6 ± 0.56 | 10.0 ± 0.47 | 8.9 ± 0.37 |
| 30 | 9.2 ± 0.42 | 9.1 ± 0.33 | 10.0 ± 0.35 | 8.8 ± 0.43 |
| 60 | 8.6 ± 0.30 | 8.2 ± 0.38 | 9.4 ± 0.34 | 9.1 ± 0.36 |
| 90 | | | | |
| 120 | 8.5 ± 0.45 | 8.3 ± 0.38 | 9.5 ± 0.37 | 9.4 ± 0.42 |
| 150 | | | | |
| 180 | 8.6 ± 0.46 | 8.4 ± 0.41 | 9.6 ± 0.38 | 9.6 ± 0.38 |

In blood anticoagulated with E/C the MPV decreased in the first 30 min and then increased. In contrast blood anticoagulated E/A, E/D and E/T the MPV decreased in the first 60 min and then remained stable.

Mean platelet component

| Time/ min | MPC in blood anticoagulated with E/A/g/dl | MPC in blood anticoagulated with E/D/g/dl | MPC in blood anticoagulated with E/T/g/dl | MPC in blood anticoagulated with E/C/g/dl |
|---|---|---|---|---|
| 0 | 24.0 ± 0.53 | 23.6 ± 0.73 | 22.8 ± 0.55 | 25.4 ± 0.47 |
| 30 | 25.0 ± 0.65 | 25.3 ± 0.63 | 23.4 ± 0.41 | 25.8 ± 0.57 |
| 60 | 25.5 ± 0.39 | 26.6 ± 0.26 | 23.9 ± 0.16 | 25.0 ± 0.38 |
| 90 | | | | |
| 120 | 26.2 ± 0.26 | 26.5 ± 0.31 | 23.9 ± 0.13 | 24.4 ± 0.28 |
| 150 | | | | |
| 180 | 26.0 ± 0.27 | 26.3 ± 0.23 | 23.6 ± 0.12 | 23.9 ± 0.15 |

In blood anticoagulated by E/C there was an increased in the MPC in the first 30 min followed by a decrease. In blood anticoagulated with E/D and E/T the MPC continued to increase up to 60 min post venesection and in blood anticoagulated with E/A the increase in MPC continued up to 120 min post venesection.

Mean platelet mass

| Time/ min | MPM in blood anticoagulated with E/A/pg | MPM in blood anticoagulated with E/D/pg | MPM in blood anticoagulated with E/T/pg | MPM in blood anticoagulated with E/C/pg |
|---|---|---|---|---|
| 0 | 2.02 ± 0.07 | 2.01 ± 0.07 | 1.99 ± 0.07 | 2.01 ± 0.08 |
| 30 | 2.07 ± 0.07 | 2.06 ± 0.07 | 2.04 ± 0.07 | 2.06 ± 0.07 |
| 60 | 2.01 ± 0.06 | 2.02 ± 0.06 | 2.00 ± 0.06 | 2.01 ± 0.06 |
| 90 | | | | |
| 120 | 2.06 ± 0.08 | 2.01 ± 0.07 | 2.02 ± 0.07 | 2.02 ± 0.07 |
| 150 | | | | |
| 180 | 2.02 ± 0.08 | 2.03 ± 0.07 | 2.01 ± 0.07 | 2.00 ± 0.07 |

The changes in MPM with time were very similar in all four coagulant combinations.

CDG2P % positive platelets

| Time/ min | CD62 % positive in blood anticoagulated with E/A | CD62 % positive in blood anticoagulated with E/D | CD62 % positive in blood anticoagulated with E/T | CD62 % positive in blood anticoagulated with E/C |
|---|---|---|---|---|
| 0 | 0.92 ± 0.47 | 1.53 ± 0.64 | 1.91 ± 0.71 | 2.11 ± 0.96 |
| 30 | 2.65 ± 1.53 | 2.85 ± 1.17 | 3.11 ± 1.50 | 2.32 ± 1.06 |
| 60 | 3.75 ± 1.86 | 4.62 ± 1.51 | 4.14 ± 1.66 | 5.14 ± 1.34 |
| 90 | | | | |
| 120 | 5.52 ± 1.89 | 6.80 ± 2.11 | 9.81 ± 3.62 | 10.41 ± 1.54 |
| 150 | | | | |
| 180 | 8.72 ± 2.48 | 9.25 ± 2.35 | 14.48 ± 3.62 | 13.44 ± 1.88 |

The number of CD62P positive platelets increased with time over the 180 min period in all four anticoagulants.

Platelet-leucocyte aggregate formation

| Time/ min | % platelet leucocyte aggregates in blood anticoagulated with E/A | % platelet leucocyte aggregates in blood anticoagulated with E/D | % platelet leucocyte aggregates in blood anticoagulated with E/T | % platelet leucocyte aggregates in blood anticoagulated with E/C |
|---|---|---|---|---|
| 0 | 2.54 ± 0.91 | 3.14 ± 0.72 | 2.77 ± 0.92 | 2.40 ± 0.61 |
| 30 | 3.08 ± 0.89 | 3.76 ± 1.13 | 2.95 ± 0.52 | 3.6 ± 0.72 |
| 60 | 3.22 ± 0.50 | 4.41 ± 1.52 | 3.00 ± 0.70 | 4.10 ± 1.13 |
| 90 | | | | |
| 120 | 4.46 ± 0.6 | 5.55 ± 1.02 | 5.54 ± 0.80 | 5.26 ± 1.00 |
| 150 | | | | |
| 180 | 7.57 ± 1.36 | 6.53 ± 0.99 | 8.16 ± 1.20 | 5.72 ± 0.97 |

The number of platelet-leucocyte aggregates increased with time in blood anticoagulated with all four combinations of anticoagulant. The lowest percentage of platelet-leucocyte aggregates at 180 min was found in blood anticoagulated with E/C.

Conclusions

In blood anticoagulated with E/C there was a decrease in MPV and increase in MPC in the first 30 min post venesection. These changes are thought to be associated with sphering of the platelets. Similar changes occurred in blood anticoagulated with E/A, E/T and E/D but over a more prolonged period of time. Since sphering of platelets is required for determining the MPV and MPC on the ADVIA 120 it is desirable that this occurs as rapidly as possible post venesection. Therefore the use of E/C is preferable to E/A, E/D or E/T for this purpose.

EXAMPLE 3

Premixing Components, Effect of Low Temperature, Full Blood Count

Materials and Methods

Materials.

Tyrodes salt solution (TS; $CaCl_2 2H_2O$ 0.265 g/L, $MgCl_2 6H_2O$ 0.214 g/L, KCl 0.2 g/L, Na $H_2CO_2$ 1.0 g/L, NaCl 8.0 g/L, $NaPO_4$ 0.05 g/L, glucose 1.0 g/L) and human thrombin (10 units) were from Sigma (Poole, Dorset, UK). $K_3EDTA$ and CTAD in Vacutainer™ containers were from BD Biosciences (Cowley, Oxford, UK); the latter were stored in light protective boxes and removed just prior to use.

Antisera.

As Example 1.

Blood Samples.

Blood was collected from the antecubital vein of seven healthy individuals (median age 35) who had not taken any medication including aspirin or aspirin containing products in the previous 48 h.

Assessment of Platelet Activation on the ADVIA® 120.

Whole blood samples were taken into Vacutainer™ containers that contained either $K_3EDTA$, or CTAD, or a mixture of $K_3EDTA$ and CTAD (E/C). For the latter, blood was collected first into $K_3EDTA$ and then immediately transferred to a Vacutainer™ containing CTAD. Samples were held at ambient temperature, analysed immediately and at 30, 60, 120, and 180 min after venesection. Analysis of platelet count (PLT), mean platelet volume (MPV) and mean platelet component concentration (MPC) was done using the ADVIA®120 haematology system (Bayer Corporation, Tarrytown, N.Y.) Platelet counts made in blood anticoagulated with CTAD and E/C were corrected for dilution (dilution factors were 1.11 and 1.125 respectively). The system was calibrated and standardised prior to use with ADVIA®-SETpoint Haematology Control and ADVIA® OPTIpoint, respectively (Bayer Corporation). In one series of experiments (n=4) these analyses were performed on blood samples anticoagulated with E/C but held at ambient temperature and at 4° C. to investigate the effect of cooling on platelet activation.

Measurement of the Expression CD62P and of the Percentage of Leucocytes that had Platelets Attached (Platelet-leucocyte Aggregates).

As Example 1.

Flow Cytometry.

As Example 1. Platelet-leucocyte aggregates could then be gated to a histogram (C) of side scatter (logarithmic scale ordinate) and orange fluorescence (logarithmic scale abscissa) to identify, by their characteristic SLS, which leucocytes were forming PLAs.

Investigation of the Inhibitory Effect of CTAD on Thrombin Activated Platelets

In one series of experiments (n=3) the effect of CTAD on platelet activation was investigated in blood anticoagulated with $K_3EDTA$ that had been incubated with a sub-optimal concentration (determined previously by titration) of human thrombin. A concentration of thrombin was chosen, to stimulate a low level of platelet activation as determined by CD62P expression. Thrombin (15 μl) was added to blood (210 μl) that had been anticoagulated with $K_3EDTA$ to give a final concentration of 0.0012 U/ml and incubated at ambient temperature with FITC-CD62P (25 μl). At 10 min, a sample (40 μl) was removed, added to CTAD (5 μl) and incubated for a further 20 min. Control blood samples anticoagulated with $K_3EDTA$ or CTAD to which no thrombin had been added were also incubated with FITC-CD62P for 30 min. Aliquots (5 μl) of blood were removed from each reaction tube at 0, 10, 20, 40 and 60 min, diluted with TS (995 μl) and analyzed immediately by flow cytometry.

Statistical Analysis.

Results from the flow cytometer and the ADVIA®120 Haematology system were compared using the paired t test, to test for significant differences between the same sample analysed at different times. To take into account multiple comparisons values of $p<0.01$ were considered significant. Results were also compared for analysis of variance (ANOVA) to test for significant differences between means and the post hoc Scheffe test was applied for multiple comparisons.

Results

Platelet Count (PLT)

Platelet counts in all three anticoagulants immediately after venesection did not differ significantly and were in the normal range. No significant changes in platelet count occurred over 180 min in blood kept with the different anticoagulants at ambient temperature (Table 1) nor when blood anticoagulated with E/C was held at 4° C.

TABLE 1

Platelet counts in blood kept with different anticoagulants.

| Time (min) | Anticoagulant | | | |
|---|---|---|---|---|
| | *EDTA | *CTAD | *E/C | **E/C at 4° C. |
| 0 | 235 ± 13 | 229 ± 14 | 230 ± 14 | 243 ± 33 |
| 30 | 246 ± 14 | 229 ± 14 | 238 ± 14 | 243 ± 30 |
| 180 | 246 ± 5 | 224 ± 7 | 225 ± 10 | 256 ± 30 |

*Mean of 7;
**Mean of 4

| | Mean Platelet Volume (MPV) | | | |
|---|---|---|---|---|
| Time/ min | MPV in blood anticoagulated with EDTA at RT/fl | MPV in blood anticoagulated with CTAD at RT/fl | MPV in blood anticoagulated with E/C at RT/fl | MPV in blood anticoagulated with E/C at 4° C./fl |
| 0 | 8.0 ± 0.37 | 9.1 ± 0.24 | 9.0 ± 0.24 | 8.8 ± 0.47 |
| 30 | 7.7 ± 0.27 | 8.4 ± 0.24 | 8.6 ± 0.32 | 8.4 ± 0.52 |
| 60 | 7.7 ± 0.24 | 8.5 ± 0.27 | 8.7 ± 0.30 | 8.1 ± 0.45 |
| 90 | | | | |
| 120 | 8.0 ± 0.30 | 8.9 ± 0.28 | 9.0 ± 0.28 | 8.22 ± 0.34 |
| 150 | | | | |
| 180 | 8.1 ± 0.21 | 9.2 ± 0.20 | 9.2 ± 0.28 | |

Values for the MPV fell initially in all anticoagulants and then rose again. When blood was kept at ambient temperature the nadir was at 30 min in all anticoagulants but was at 60 min when blood anticoagulated with E/C was kept at 4° C. When stored at ambient temperature, the MPV values at all times were significantly lower ($p<0.04$) in blood that had been anticoagulated with $K_3EDTA$ than in blood anticoagulated with CTAD or E/C.

| | Mean Platelet Component (MPC) | | | |
|---|---|---|---|---|
| Time/ min | MPC in blood anticoagulated with EDTA at RT/pg/l | MPC in blood anticoagulated with CTAD at RT/pg/l | MPC in blood anticoagulated with E/C at RT/pg/l | MPC in blood anticoagulated with E/C at 4° C./pg/l |
| 0 | 28.0 ± 0.87 | 25.2 ± 0.62 | 25.6 ± 0.54 | 25.1 ± 0.78 |
| 30 | 29.1 ± 0.52 | 27.1 ± 0.40 | 26.6 ± 0.66 | 27.0 ± 0.25 |
| 60 | 28.8 ± 0.42 | 26.7 ± 0.40 | 26.4 ± 0.64 | 27.4 ± 0.19 |
| 90 | | | | |
| 120 | 27.9 ± 0.48 | 26.3 ± 0.67 | 25.4 ± 0.67 | 27.0 ± 0.21 |
| 150 | | | | |
| 180 | 27.1 ± 0.36 | 25.2 ± 0.40 | 25.0 ± 0.67 | |

In direct contrast to the results for MPV values (above), the MPC values rose initially and then fell. Maximal values were reached at 30 min in all anticoagulants when blood was kept at ambient temperature and at 60 min when it was kept in E/C at 4° C. Mean platelet component values were significantly higher at all times in blood kept at ambient temperature with $K_3$EDTA than with CTAD (p<0.04) or E/C (p<0.02).

| | Expression of CD62P on platelets | | | |
|---|---|---|---|---|
| Time/ min | CD62P % positive platelets in blood anticoagulated with EDTA at RT | CD62P % positive platelets in blood anticoagulated with CTAD at RT | CD62 % positive platelets in blood anticoagulated with E/C at RT | CD62 % positive platelets in blood anticoagulated with E/C at 4° C. |
| 0 | 1.10 ± 0.24 | 1.22 ± 0.26 | 1.28 ± 0.37 | 0.53 ± 0.12 |
| 30 | 3.71 ± 1.04 | 1.42 ± 0.37 | 2.01 ± 0.61 | |
| 60 | 11.27 ± 1.60 | 3.09 ± 0.84 | 5.94 ± 2.90 | 0.38 ± 0.17 |
| 90 | | | | |
| 120 | 18.94 ± 2.53 | 2.38 ± 0.29 | 6.98 ± 1.48 | 0.61 ± 0.34 |
| 150 | | | | |
| 180 | 23.05 ± 2.79 | 4.14 ± 0.61 | 8.45 ± 0.86 | 1.07 ± 0.57 |

Only low percentages of platelets expressed CD62P shortly after venesection (1.10±0.61%, 1.22±0.62 and 1.28±0.85, (mean±SE) in $K_3$EDTA, CTAD and E/C respectively) but the percentages ropse when blood was kept at ambient temperature. Rises at 180 min were greater in blood anticoagulated with $K_3$EDTA (23.05±1.54%) with E/C (8.45±0.79%), and were least in blood anticoagulated with CTAD (4.14±0.79%). At 180 min the percentage of CD62P positive platelets in blood anticoagulated with $K_3$EDTA was significantly higher (p<0.01) than in blood anticoagulated with CTAD or E/C. When blood samples anticoagulated with E/C were kept at 4° C., there were only minimal and non significant increases in the number of CD62P positive platelets from 0.53±0.12% at 0 min to 1.07±0.57% at 180 min.

| | Platelet-leucocyte aggregate (PLA) formation | | | |
|---|---|---|---|---|
| Time/ min | % platelet leucocyte aggregates in blood anticoagulated with EDTA at RT | % platelet leucocyte aggregates in blood anticoagulated with CTAD at RT | % leucocyte aggregates in blood anticoagulated with E/C at RT | % leucocyte aggregates in blood anticoagulated with E/C at 4° C. |
| 0 | 3.30 ± 0.5 | 3.95 ± 0.73 | 2.82 ± 0.67 | 2.82 ± 0.65 |
| 30 | 4.16 ± 0.86 | 5.57 ± 1.36 | 3.13 ± 0.86 | 3.13 ± 0.67 |
| 60 | 8.87 ± 1.54 | 9.64 ± 1.41 | 4.48 ± 0.94 | 3.29 ± 0.57 |
| 90 | | | | |
| 120 | 8.50 ± .44 | 15.80 ± 2.5 | 6.18 ± 2.28 | 3.61 ± 1.25 |
| 150 | | | | |
| 180 | 13.50 ± 1.74 | 18.88 ± 2.06 | 7.81 ± 1.43 | 3.91 ± 1.40 |

Immediately after venesection, a small percentage of leucocytes that were associated with platelets could be found in blood from all donors irrespective into which anticoagulant it had been collected (3.50±0.71%, 3.95±0.97% and 2.82±1.05% (mean±SE) in $K_3$EDTA, CTAD and E/C respectively). In all anticoagulants, the percentage of platelet-leucocyte aggregates rose markedly when blood was kept at ambient temperature. The increases at 180 min were greater in blood anticoagulated with CTAD (18.88±2.06%) than with $K_3$EDTA (13.50±1.74%) and were least in blood that had been anticoagulated with E/C (7.81±1.43%). However when blood samples anticoagulated with E/C were incubated at 4° C. there were only minimal increases in the percentage of platelet-leucocyte aggregates over 180 min.

The Effect of CTAD on Thrombin Activated Platelets

To ascertain whether CTAD could effectively inhibit further responses by platelets that had already encountered an agonist, blood that had been collected into $K_3$EDTA was incubated alone or with a sub-optimal concentration of thrombin. After 10 min an aliquot of the thrombin-stimulated blood was added to CTAD. Platelet activation, as monitored by CD62P expression, was completely inhibited by the addition of CTAD, whereas progressive activation occurred in blood that had been anticoagulated only with $K_3$EDTA and, as expected, was greater in these samples when thrombin had been added than when it had been omitted.

Investigation of the Stability of EDTA and CTAD when Mixed Prior to Use

Because the results so far suggested that E/C might be a better anticoagulant for platelet studies than either $K_3$EDTA or CTAD alone, the effect of pre-mixing the two components was investigated. Blood was collected into mixtures of $K_3$EDTA and CTAD that had been prepared either 14 days or just immediately prior to use and into $K_3$EDTA that was then mixed with CTAD (as had been done previously throughout the study). All samples were kept subsequently at 4° C. Values for routine haematological and platelet activation parameters measured on the ADVIA®120 soon after venesection were similar irrespective whether the two anticoagulants were mixed before or after blood collection. Moreover the values remained essentially unchanged when analysed also at 3, 6 and 24 h. Immunofluorescence assays showed that the percentage of leucocytes involved in aggregates with platelets rose slightly (<5% increases at 24 h) in all samples (results not shown) over 24 h.

Comparison of ADVIA®120 Haematology Results in Blood Anticoagulated with EDTA, CTAD and E/C.

To investigate whether blood anticoagulated with E/C could be used for routine analysis of haematological parameters the results obtained on the ADVIA®120 from 7 control samples anticoagulated with EDTA, CTAD and E/C were compared. There were no significant differences in the measurement of the white blood cell counts (WBC) the red cell counts (RBC) and the haemoglobin (HGB) concentration in blood samples anticoagulated with the three anticoagulants. However the haematocrit and a number of the platelet parameters were significantly different (p<0.01) in blood anticoagulated with CTAD and E/C compared to that anticoagulated with EDTA (Table 2).

activation. MPC values in blood anticoagulated with CTAD or E/C were similar over 180 min and were significantly lower than in $K_3$EDTA. Taken together, the changes in MPV and MPC values at ambient temperature suggest that in blood anticoagulated with E/C, the platelets become sphered (although perhaps not maximally), without undergoing degranulation. This is confirmed by the low level of expression of CD62P on platelets in E/C anticoagulated blood, which was comparable to that on platelets in blood anticoagulated with CTAD alone.

As yet, it is not clear why at ambient temperature the percentage of platelets expressing CD62P in blood anticoagulated with CTAD fell slightly between 60 and 120 min but a possible explanation is that some activated platelets

TABLE 2

Comparison of ADVIA ® 120 haematology results in blood anticoagulated with EDTA, CTAD and E/C.

| Parameter | SI Unit | Mean (+/-S.E.) at 30 minutes | | |
|---|---|---|---|---|
| | | EDTA | CTAD (×1.11) | E/C (×1.125) |
| PLT | 109/L | 246 (14) | 229 (14) | 238 (14) |
| MPV | fL | 7.7 (0.27) | *8.4 (0.24) | *8.6 (0.32) |
| PDW | % | 58.9 (3.24) | *53.8 (2.40) | 55.6 (2.24) |
| PCT | % | 0.19 (0.01) | *0.17 (0.01) | 0.18 (0.01) |
| MPC | g/dL | 29.1 (0.52) | *27.1 (0.40) | *26.6 (0.66) |
| PCDW | g/dL | 5.00 (0.09) | *7.2 (0.13) | *6.9 (0.38) |
| WBC | 109/L | 5.35 (0.40) | 5.27 (0.42) | 5.36 (0.40) |
| NEUTROPHIL | 109/L | 3.13 (0.24) | 3.07 (0.24) | 3.10 (0.22) |
| LYMPHOCYTE | 109/L | 1.61 (0.20) | 1.65 (0.23) | 1.69 (0.24) |
| MONOCYTE | 109/L | 0.32 (0.04) | 0.28 (0.03) | 0.30 (0.04) |
| EOSINOPHIL | 109/L | 0.11 (0.04) | 0.12 (0.04) | 0.11 (0.03) |
| BASOPHIL | 109/L | 0.06 (0.01) | 0.03 (0.01) | 0.04 (0.01) |
| RBC | 106/microliter | 4.77 (0.20) | 4.82 (0.21) | 4.87 (0.21) |
| HGB | g/dL | 14.7 (0.40) | 14.8 (0.40) | 15.1 (0.44) |
| HCT | L/L | 0.421 (0.01) | *0.434 (0.01) | *0.438 (0.01) |
| MCV | fL | 88.7 (1.82) | *90.5 (1.89) | *90.4 (1.93) |
| MCH | pg | 30.9 (0.56) | 30.9 (0.63) | *31.1 (0.56) |
| MCHC | g/dL | 34.9 (0.20) | *34.2 (0.20) | *34.4 (0.23) |
| RDW | % | 12.5 (0.10) | 12.6 (0.11) | 12.6 (0.12) |

*Indicates significant differences P < 0.01 between EDTA and anticoagulant.

Discussion

Data presented here clearly show that the MPV in EDTA, CTAD and E/C fell between 0–30 minutes but then rose again. The results for EDTA are largely in agreement with those of previous studies in which MPV was determined by optical procedures (Trowbridge, E. A., Reardon, D. M., Hutchinson, D., Pickering, C. (1985) "The routine measurement of platelet volume. A comparison of light-scattering and aperture-impedance technologies." Clin. Phys. Physiol. Meas. 6, 221–238).

Consistent with recent reports, CTAD largely inhibited the increases in expression of CD62P that occurred on platelets kept for 180 min at ambient temperature in blood anticoagulated with $K_3$EDTA (Kuhne et al. 1995; Macey et al., 1999; Mody et al., 1999). Furthermore, when blood that had been anticoagulated with $K_3$EDTA was stimulated with thrombin, the subsequent addition of CTAD inhibited platelet degranulation and the increases in CD62P expression that otherwise occurred in blood kept with just $K_3$EDTA. We have previously demonstrated that following in vitro stimulation of $K_3$EDTA anticoagulated whole blood, increases in CD62P expression are accompanied by a concurrent decrease in MPC (Macey et al., 1999). We now show that at ambient temperature, the MPC decreased in $K_3$EDTA more than in CTAD or E/C, confirming that EDTA causes platelet had adhered to the tube wall or to other leucocytes in the blood. In fact, blood anticoagulated with CTAD contained higher numbers of platelet-leucocyte aggregates than did blood that had been anticoagulated with $K_3$EDTA or E/C. The reasons for this are not immediately apparent but seem dependent on the presence of EDTA. Somewhat paradoxically, EDTA has been shown to affect platelet membrane-bound receptors in a way that enhances rather than diminishes granule secretion and aggregation (Golanski, J., Pietrucha, T., Baj, Z., Greger, J., Watala, C. (1996) "Molecular insights into the anticoagulant-induced spontaneous activation of platelets in whole blood—various anticoagulants are not equal". Thrombosis Research 83, 199–216). However external $Ca^{2+}$ is required for aggregation and as EDTA is a better chelator of $Ca^{2+}$ than citrate it may have a greater inhibitory effect in these respects. If this explanation is true, then it is possible that CTAD might not completely inhibit increases in CD62P expression, as activated platelets could be present but remain undetected, because they were attached to leucocytes. These results suggest that platelet-leucocyte aggregate formation should be monitored during studies of platelet activation in whole blood and also highlight the fact that ex vivo platelet-leucocyte aggregate formation is anticoagulant-dependent.

The crucial finding of this study is that when blood was anticoagulated with E/C and held at 4° C. there were minimal changes in the parameters of platelet activation for at least 180 min. This finding will be important for clinical studies, because three hours is usually sufficient time for a sample taken in the wards or the clinic to reach the laboratory for analysis. In fact, preliminary studies indicate that this time period could probably be safely extended to six hours. Presumably the inhibitory effects of CTAD on intracellular calcium mobilisation prevent granule release and subsequent PLA formation.

Figure 3:
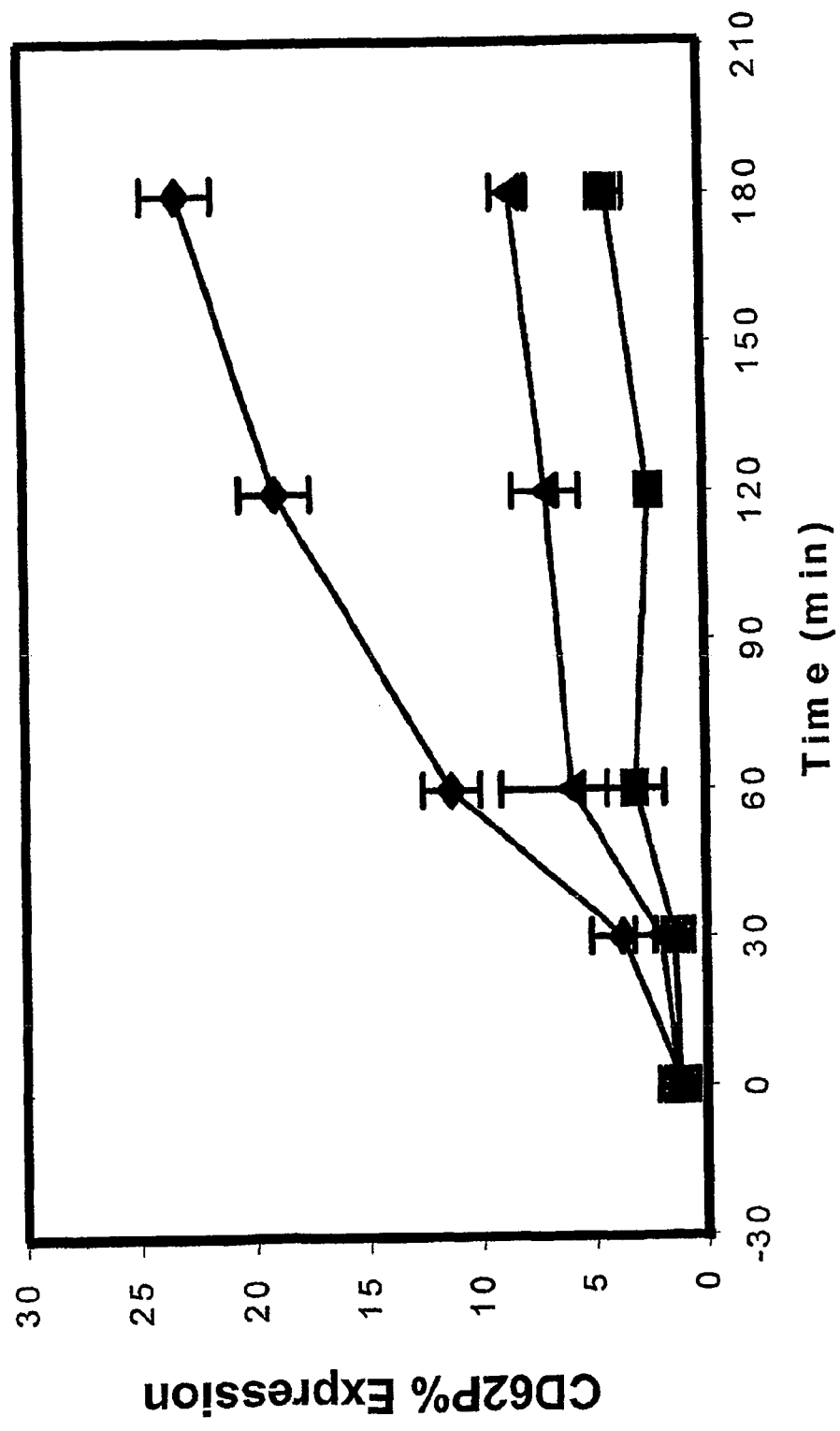
FIG. 3 shows the analysis of platelet leucocyte aggregates in whole blood. Blood was stained with phycoerythrin-conjugated CD45 and fluorescein isothiocyanate-conjugated CD42a. Leucocytes were identified (region RI) by their positive staining with PE CD45 in a plot of side scatter (logarithmic scale ordinate) versus orange fluorescence (logarithmic scale abscissa) (dot plots A) and were displayed in a plot of green fluorescence (logarithmic scale ordinate) and orange fluorescence (logarithmic scale abscissa) (dot plots B). Events that were both green (CD42a) and orange (CD45) (region R2) were considered platelet leucocyte aggregates. Back gating these events to a plot of side scatter (logarithmic scale ordinate) versus orange fluorescence (logarithmic scale abscissa) (dot plot C) showed that the majority of aggregates had the side light scatter characteristics of granulocytes and monocytes. An example of the analysis performed on blood from a normal control is illustrated in the upper panel and that from a patient with inflammatory bowel disease in the lower panel.

It is known that the inhibitory effects of the platelet antagonists in CTAD begin to dissipate at 3–4 h when blood is kept at ambient temperature and, if necessary, storage times could probably be prolonged by increasing their concentration (2) Mody et al., 1999). Under the conditions described here (of time and temperature) E/C effectively spheres platelets without simultaneously causing degranulation, thereby allowing the accurate measurement of MPC on the ADVIA®120. The ability of E/C also to inhibit platelet-leukocyte aggregate formation ex vivo, indicates that this combined anticoagulant is suitable for the investigation of these interactions in clinical studies. Indeed, we have recently found that in blood samples anticoagulated with E/C there are significantly greater numbers of platelet-leucocyte aggregates (5.16±1.48, mean±SE) in the blood of patients (n=62) with inflammatory bowel disease than in normal controls (n=20) (3.43±0.82, mean±SE, p=0.03) (unpublished data, an example of which is illustrated in FIG. 3). It also appears that the combined anticoagulant E/C would be suitable for the routine analysis of the majority of haematology parameters on the ADVIA®120. However, from a clinical point of view, it is not practical to take blood into one Vacutainer™ and then pour it into a second, or to mix the contents of two Vacutainer™ containers. For this reason tubes containing both anticoagulants are preferable.

In conclusion, the above results show that CTAD/EDTA mixture provides significant advantages for measuring ex vivo platelet activation and for measuring ex vivo leucocyte activation.

What is claimed is:

1. A method of measuring leucocyte activation, comprising measuring a leucocyte activation indicator of leucocytes suspended in a blood anticoagulant composition comprising one or more components for effecting platelet sphering, and two or more of:
    (a) theophylline,
    (b) adenosine and/or 2-chloroadenosine,
    (c) dipyridamole, and
    (d) citrate.

2. A method of measuring platelet activation, comprising determining mean refractive index of blood platelets suspended in a composition comprising at least one component for effecting platelet sphering comprising EDTA, EGTA or a combination thereof, and at least one platelet antagonist.

3. The method of claim 2, wherein said at least one platelet antagonist comprises:
    a) theophylline,
    b) adenosine and/or 2-chloroadenosine, or
    c) dipyridamole.

4. The method of claim 2, wherein said at least one platelet antagonist comprises two or more of
    a) theophylline,
    b) adenosine and/or 2-chloroadenosine, and
    c) dipyridamole.

5. The method of claim 2, wherein said at least one platelet antagonist comprises:
    a) theophylline,
    b) adenosine and/or 2-chloroadenosine, and
    c) dipyridamole.

6. The method of claim 2, wherein said at least one platelet antagonist comprises:
    a) theophylline,
    b) adenosine, and
    c) dipyridamole.

7. The method of any one of claims 3 to 6 wherein the composition further comprises citrate.

8. The method of claim 2, wherein said component for effecting platelet sphering comprises EDTA, said at least one platelet antagonist comprises theophylline, adenosine and dipyridamole and said composition further comprises citrate.

9. The method of claim 2, wherein the mean refractive index is determined by measuring light scatter at two different angles to an incident light beam.

10. The method of claim 9, wherein the two different angles are angles of 2–3 degrees and 5–15 degrees to the direction of the incident light beam.

11. The method of claim 2, wherein said refractive index determination is carried out at a time of from 30 to 60 minutes after a venesection.

12. The method of claim 2, wherein an anticoagulated blood sample is maintained at a temperature of 0°C. to 10°C. between a venesection and said determining.

13. The method of claim 1, wherein the two or more other components comprise three or more of
    a) theophylline,
    b) adenosine and/or 2-chloroadenosine,
    c) dipyridamole, and
    d) citrate.

14. The method of claim 1, wherein the two or more other components comprise
    a) theophylline,
    b) adenosine and/or 2-chloroadenosine,
    c) dipyridamole, and
    d) citrate.

15. The method of any one of claims 1, 13 and 14, wherein the one or more components for effecting platelet sphering comprises a chelating agent.

16. The method of claim 15, wherein the chelating agent is one or both of EDTA and EGTA.

17. The method of claim 16, wherein the blood anticoagulant composition comprises a mixture of EDTA and CTAD.

18. A method of maintaining a blood sample in an anticoagulated state between venesection and measurement of platelet activation, comprising preparing a composition comprising a whole blood sample and a blood anticoagulant composition comprising EDTA or EGTA or a combination thereof, and CTAD.

19. A blood anticoagulant composition comprising one or more components for effecting platelet sphering comprising EDTA or EGTA, or a combination thereof, and wherein said composition also comprises citrate, theophylline, dipyridamole, and adenosine and/or 2-chloroadenosine.

20. The composition of claim 19, which comprises EDTA and CTAD.

21. A method of measuring leucocyte activation, comprising measuring a leucocyte activation indicator of leucocytes suspended in a blood anticoagulant composition comprising one or more components for effecting platelet sphering including EDTA and/or EGTA; and:

(a) theophylline,
(b) adenosine and/or 2-chloroadenosine, and
(c) citrate.

22. A blood anticoagulant composition comprising one or more components for effecting platelet sphering including EDTA and/or EGTA; and:
(a) theophylline,
(b) adenosine at a concentration of 0.01 mM to 3.7 mM,
(c) citrate, and
(d) dipyridamole.

23. The composition of claim 22 comprising a mixture of EDTA and CTAD.

24. A method of measuring platelet count, wherein platelet count is measured on platelets suspended in an anticoagulant composition of claim 19 or claim 22.

25. A method of measuring platelet activation, comprising measuring a platelet activation indicator of platelets suspended in the anticoagulant composition of claim 19 or claim 22.

26. The method of claim 25, wherein an anticoagulated blood sample is maintained at a temperature of 0°C. to 10°C. between a venesection and a measurement.

27. The method of claim 25, wherein the method comprises measuring CD62P expression of the platelets.

28. The method of claim 25, wherein the method comprises determining the mean refractive index of the platelets.

29. The method of claim 28, wherein the mean refractive index is determined by measuring light scatter at two different angles to an incident light beam.

30. The method of claim 29, wherein the two different angles are angles of 2–3 degrees and 5–15 degrees to the direction of the incident light beam.

31. The method of claim 28, wherein said refractive index determination is carried out at a time of from 30 to 60 minutes after a venesection.

32. A method of maintaining a blood sample in an anticoagulated state between venesection and measurement of platelet activation, comprising preparing a composition comprising a blood sample and the blood anticoagulant composition of claim 19 or claim 22.

* * * * *